US012812988B2

(12) United States Patent
Bardash

(10) Patent No.: US 12,812,988 B2
(45) Date of Patent: Nov. 24, 2026

(54) SOLID STATE DETECTOR FOR VERY HIGH DOSE RATE RADIATION

(71) Applicant: Michael Bardash, Brooklyn, NY (US)

(72) Inventor: Michael Bardash, Brooklyn, NY (US)

( * ) Notice: Subject to any disclaimer, the term of this patent is extended or adjusted under 35 U.S.C. 154(b) by 107 days.

(21) Appl. No.: 18/759,984

(22) Filed: Jun. 30, 2024

(65) Prior Publication Data

US 2025/0006857 A1 Jan. 2, 2025

Related U.S. Application Data

(60) Provisional application No. 63/511,169, filed on Jun. 29, 2023.

(51) Int. Cl.

| | |
|---|---|
| ***H10F 30/295*** | (2025.01) |
| ***A61N 5/10*** | (2006.01) |
| ***G01T 1/24*** | (2006.01) |
| ***H10F 77/122*** | (2025.01) |
| ***H10F 77/20*** | (2025.01) |

(52) U.S. Cl.
CPC ......... *H10F 30/295* (2025.01); *A61N 5/1071* (2013.01); *G01T 1/241* (2013.01); *H10F 77/122* (2025.01); *H10F 77/241* (2025.01)

(58) Field of Classification Search
CPC ..... H10F 30/295; H10F 77/241; H10F 77/122
See application file for complete search history.

(56) References Cited

U.S. PATENT DOCUMENTS 8,350,225 B1 * 1/2013 Bardash ................ H10K 39/30
250/370.07

* cited by examiner

*Primary Examiner* — Hugh Maupin
(74) *Attorney, Agent, or Firm* — Stoyanov Law PLLC; Roy Chan

(57) ABSTRACT

A solid state detector for ionizing radiation having a semiconductor substrate, a conductive metal layer, a first and a second active region, the first active region having a faster response time to ionizing radiation than the second active region. A first voltage is applied to the first active region and a second voltage applied to the second active region, the first and second voltages having opposite polarities and equal magnitudes. The solid state detector being configured to maintain a constant output voltage when not irradiated and to output an output voltage when irradiated, the output voltage being the time resolved sum of a first charge and a second charge accumulated by the two active regions, the first charge and the second charge having opposite polarities and configured to drain residual charges from the active regions.

8 Claims, 8 Drawing Sheets

SOLID STATE DETECTOR FOR VERY HIGH DOSE RATE RADIATION

CROSS-REFERENCE TO RELATED APPLICATIONS

The present application claims priority to provisional U.S. patent application Ser. No. 63/511,169, filed Jun. 29, 2023, and entitled "Solid State Detector for Very High Dose Rate Radiation," the disclosure of which is incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The present invention relates to solid state detectors for ionizing radiation capable of measuring very high doses of radiation delivered over in very short pulses, for example as in FLASH (Fast Low Angle Shot) radiotherapy.

BRIEF SUMMARY OF THE INVENTION

An embodiment of a solid state detector for ionizing radiation according to the present invention comprises a substrate, a conductive metal layer deposited on the substrate, a first active region connected to a first input lead and a first output lead, a second active region connected to a second input lead and a second output lead, and an output electrode. The first active region, the first input lead, the first output lead, the second active region, the second input lead, the second output lead, and the output electrode are formed in the metal layer. The first output lead, the second output lead, and the output electrode are electrically connected. The first active region is configured to have a first response time when irradiated with ionizing radiation and the second active region is configured to have a second response time when irradiated with the ionizing radiation. A first voltage is applied to the first input lead and a second voltage is applied to the second input lead, the first voltage being positive, the second voltage negative, and the first voltage and the second voltage having equal magnitudes. The solid state detector is configured, when not being irradiated with ionizing radiation, to maintain an output voltage at a constant level at the output electrode, to prevent the first active region from accumulating a first charge on the first output lead, and to prevent the second active region from accumulating a second charge on the second output lead. The solid state detector is configured, when being irradiated with ionizing radiation, to cause the first output lead to accumulate the first charge at the first response time and the second output lead to accumulate the second charge at the second response time, and to output a sum of the first charge and the second charge as the output voltage at the output electrode. The first charge is positive and the second charge is negative, and when the ionization radiation is removed, the solid state detector is configured to enable the first or the second charge to drain a residual charge from the first or second active regions, and to return the output voltage to the constant level.

In another embodiment of the solid state detector for ionizing radiation the first response time is faster than the second response time, the first active region comprises a first metal pattern of digits having a first digit width and a first interdigital spacing, the first metal pattern is electrically connected to the first input lead and the first output lead, the second active region comprises a second metal pattern of digits having a second digit width and a second interdigital spacing, and the second metal pattern is electrically connected to the second input lead and the second output lead. The substrate is configured to be an insulator when the solid state detector is not being irradiated, and to generate electrical charge carriers in the substrate when the solid state detector is irradiated with ionizing radiation.

In yet another embodiment the second active region is larger than the first active region.

In another embodiment the second interdigital spacing is larger than the first interdigital spacing.

In yet another embodiment the first active region has a first diameter, the second active region has a second diameter, and the second diameter is larger than the first diameter.

In another embodiment the output voltage is representative of an amount of the ionizing radiation incident on the solid state detector during a delay time, the delay time being a time difference between the first response time and the second response time.

In yet another embodiment the substrate is a diamond substrate, and the first metal pattern of digits and the second metal pattern of digits comprise gold.

In another embodiment the metal layer is deposited on the substrate through electron beam deposition.

BRIEF DESCRIPTION OF THE SEVERAL VIEWS OF THE DRAWING

The advantages and features of the present invention will be better understood as the following description is read in conjunction with the accompanying drawings, wherein.

Figure 1:
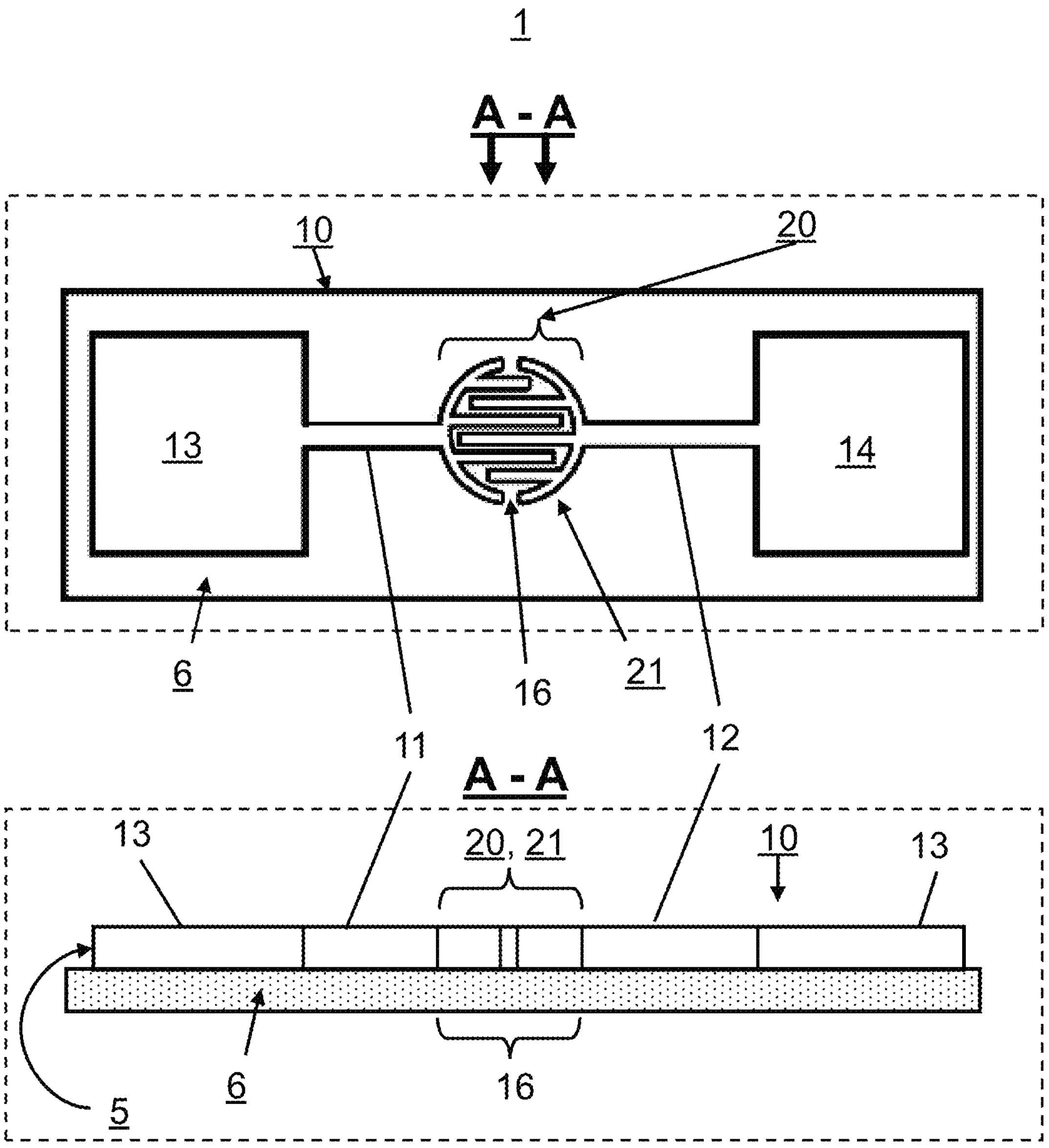
FIG. 1 is an illustration of different views of an embodiment of a solid state detector.

For clarity all reference numerals may not be included in every Figure.

DETAILED DESCRIPTION OF THE INVENTION

Embodiments of a solid state detector 1 for ionizing radiation according to the present invention comprise Metal-Semiconductor-Metal ("MSM") devices 10 capable of detecting and measuring high dose rate of radiation, such as in FLASH radiotherapy. Embodiments of MSM device 10 can be configured according to the present invention, by optimizing physical feature size, geometry, and materials, to measure high speed pulses and to reduce or overcome various challenges.

FIG. 1 illustrates a solid state detector 1 (exemplified by a dashed line) comprising an MSM device 10 from a top view, and a side view (indicated with "A-A"). FIG. 1 illustrates an embodiment of an MSM device 10 comprising a conductive metal layer 5 deposited on substrate 6 (illustrated with a dotted pattern in the "A-A" side view), an active region 20, connecting pads 13, 14, and conductive leads including input lead 11 and output lead 12. Active region 20 comprises an interdigitated metal pattern 21 of digits 22 (or fingers 22). Metal pattern 21 has an interdigital spacing 23, or in other words, digits 22 are spaced apart on top of the substrate at a pitch 23 (interdigital spacing 23 and pitch 23 are used interchangeably). Digits 22 have a digit width 25. Pads 13, 14, leads 11, 12, and metal pattern 21 a formed from, or in, metal layer 5 and form a form metal region 15. Interdigital spacing 23 forms an interdigitated substrate region 16 in substrate 6. Metal pattern 21 may comprise a plurality of input digits 22*a* electrically connected to input lead 11 and a plurality of output digits 22*b* electrically connected to output lead 12. For avoidance of doubt, the terms input, output, first, second, and similar terms or designations are not intended as limiting, are used to illustrate the described embodiments, and interchangeable in when applied to different embodiment of the present invention.

Figure 2:
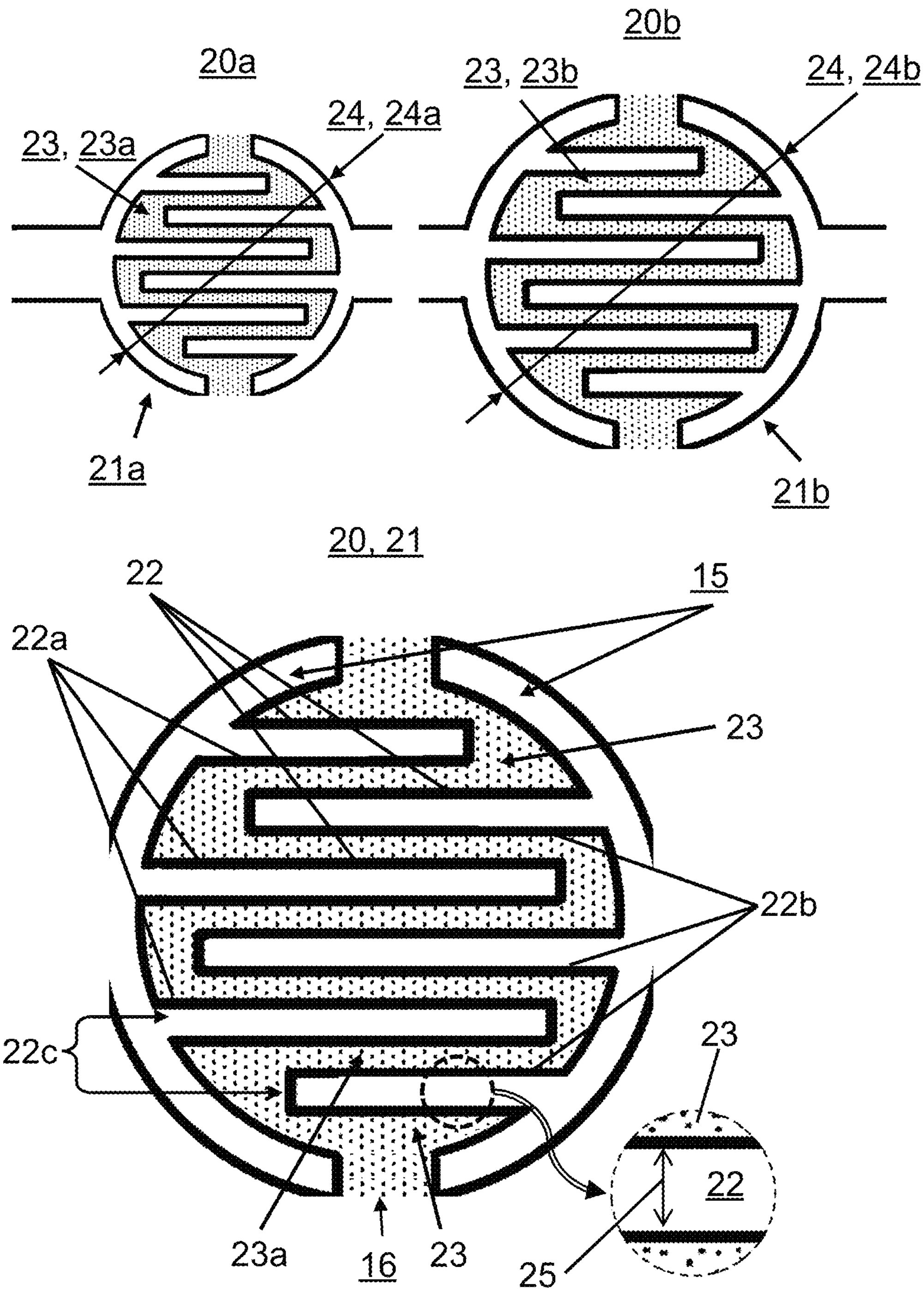
FIG. 2 is a diagram illustrating active regions according to embodiments of the invention.
Figure 3:
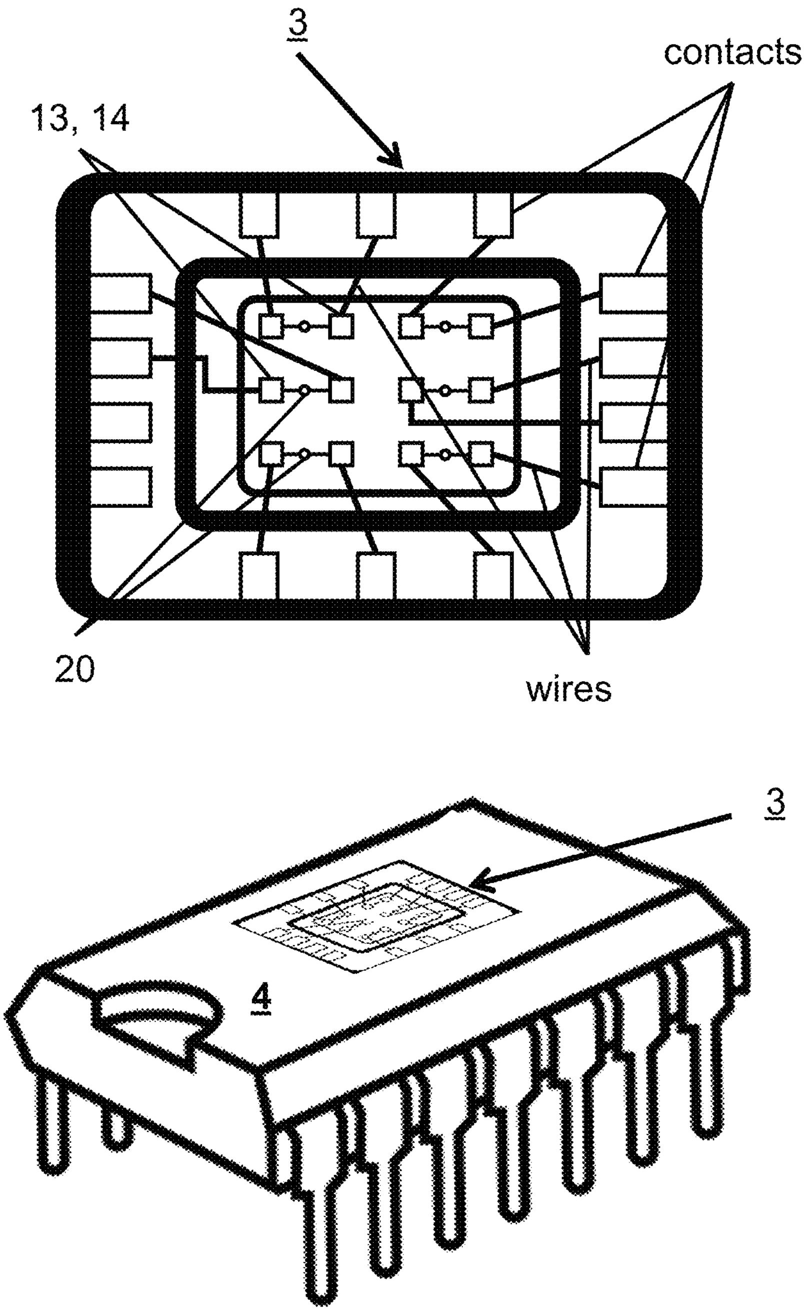
FIG. 3 is an illustration of aspects of an embodiment of an MSM device according to the invention.
Figure 4:
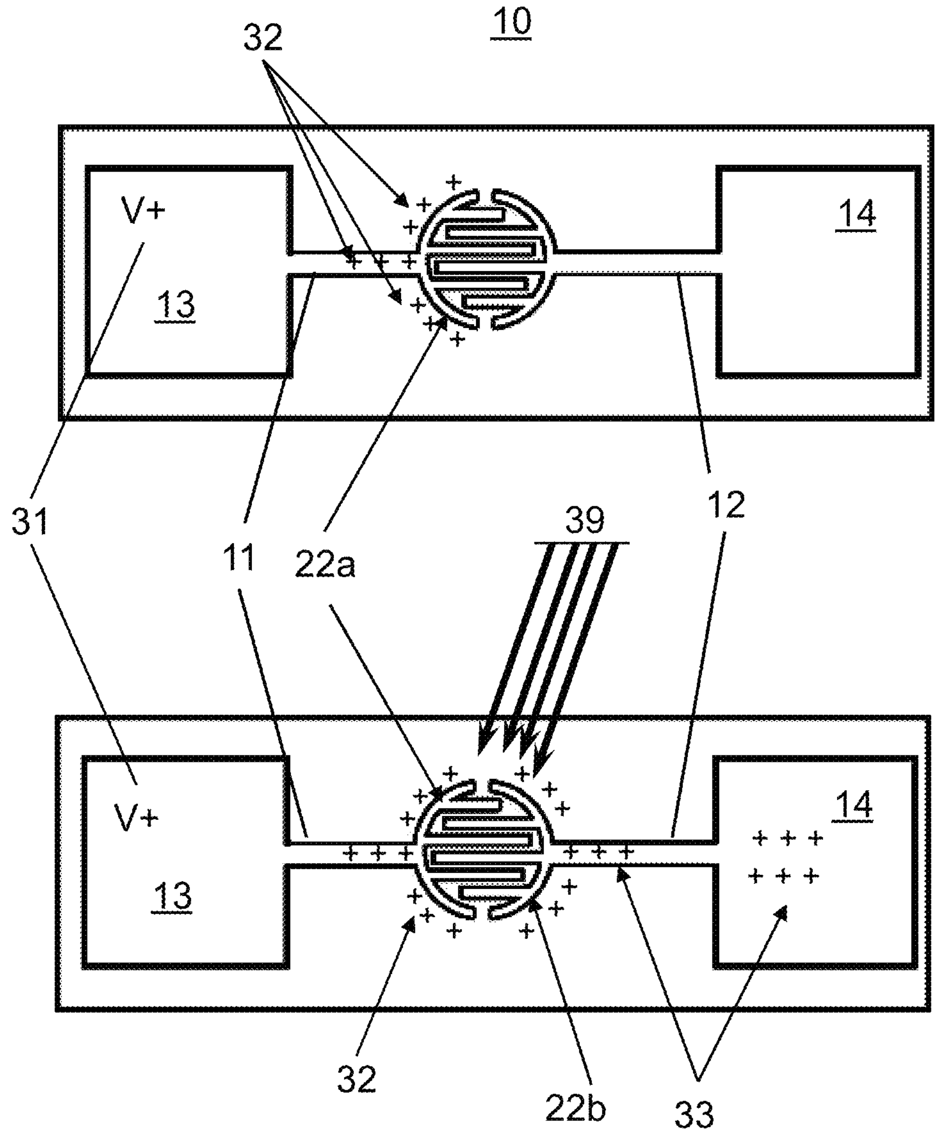
FIG. 4 is an illustration of aspects of an embodiment of an MSM device according to the invention.

FIG. 2 illustrates two embodiments of active region 20, a smaller active region 20*a* having metal pattern 21*a* and a larger active region 20*b* having metal pattern 21*b*, and an enlarged view of active region 20. FIG. 3 illustrates a configuration 3 (or package 3) of six packaged and bonded MSM devices 10 and the six-MSM-device configuration 3 packaged in a standard 14-pin chip package 4. FIG. 3 illustrates bonding pads 13, 14 connecting to external contacts via wires.

In a preferred embodiment of MSM device 10 for a fast radiation detection system according to the present invention, substrate 6 is a diamond substrate 6 and interdigitated metal pattern 21 comprises conductive digits 22 formed from gold, gold/chrome alloy, or similar. Metal layer 5 may be deposited on substrate 6 using various techniques, but preferably, electron beam deposition resulting in reduction of metal waste and relatively higher production rates due to the process's high material utilization efficiency and faster depositions rates. Digit width 25 preferably is approximately one micron (1 μm) and interdigital spacing 23 preferably is about two microns (2 μm), but may be smaller, or as large as 25 microns. Lead 11 may terminates at bonding pad 13 and lead 12 terminates in bonding pad 14. MSM device 10 may be fabricated from diamond substrate 6 leveraging diamond's characteristics, such as high carrier mobility, durability, hardness, and other characteristics. Diamond substrate 6 may be configured by selecting diamond material (e.g., based on clarity) with sufficiently large grain size to minimize grain boundaries (e.g., minimize grain boundary densities) within diamond substrate 6, and preferably within interdigitated substrate region 16. Most preferably, diamond material for diamond substrate 6 is selected with sufficiently low grain boundary density (sufficiently large grain size) so that individual interdigital spacing 23 between adjacent fingers 22 is situated on a single diamond grain.

Figure 5:
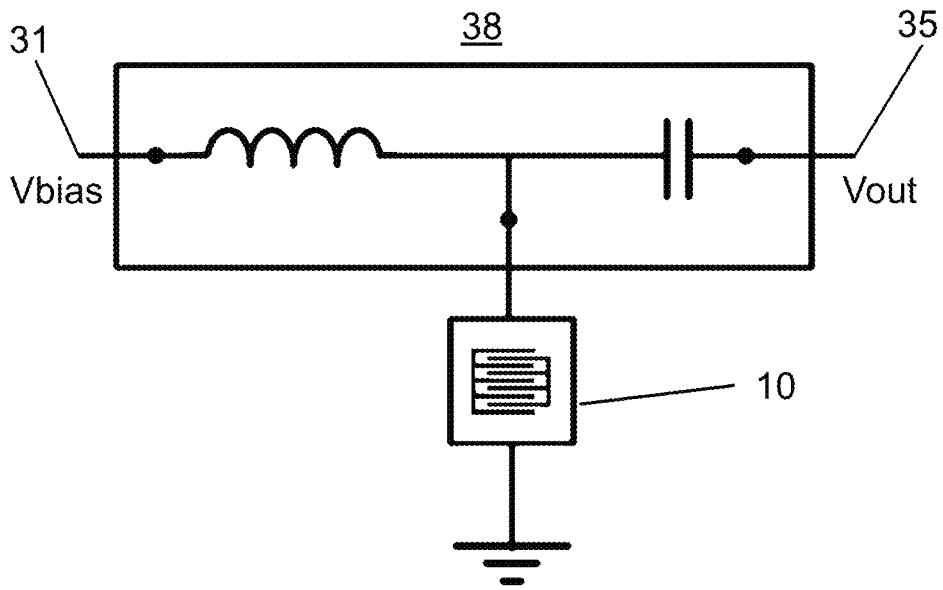
FIG. 5 is an illustration of an embodiment of the present invention.

FIG. 5 illustrates an embodiment of MSM device 10 without ionizing radiation, under normal conditions, and MS device 10 irradiated with ionizing radiation 39. Voltage 30 (V+) applied at bonding pad 13 (e.g., across bonding pads 13 and 14, by an external power source) creates an input charge 32 (depicted as "+++") at lead 11 and input digits 22*a* of active region 20. Input charge 32 generates an electric field (not shown) in interdigital substrate region 16. Substrate 6 may be configured by using substrate material (e.g. diamond) that is an insulator at normal conditions, when not irradiated, and that forms electrical charge carriers when subjected to ionizing radiation. Accordingly, when not irradiated substrate 6 can act as an insulator and such configuration prevents electrical charge 32 from accumulating at output digits 22*b*, output lead 12, and output bonding pad 14. Substrate 6, when acting as an insulator, can prevent charges 32 from crossing the interdigital spacing 23 between digits 22 and spread to output digits 22*b*, output lead 12, and output bonding pad 14. In embodiments comprising diamond substrate 6 with sufficiently large grains, substrate 6 is an insulator at ambient conditions (e.g., not irradiated, room temperature, not heated) and no current flows (i.e. no charges cross interdigital space 23 between adjacent digits 22*c*) and effectively there are no free charge carriers in diamond substrate 6.

Diamond has a high charge mobility with combined electron and hole mobility reportedly exceeding 4,000 $cm^2 \cdot V^{-1} \cdot sec^{-1}$ (four thousand square centimeters per volt-second or $cm^2/V \cdot sec$) under certain conditions. Embodiments of the present invention preferably utilize diamond substrate with sufficiently high charge carrier mobility at or above approximately 2,000 $cm^2/V \cdot sec$ (two thousand square centimeters per volt-second) at about 10 Volts applied to leads 11, 12. In an embodiment of diamond MSM device 10 a voltage 30 (e.g., V.bias, V+) applied across leads 11, 12 may result in an electric field near the surface of substrate 6 without current flowing between input lead 11 and output lead 12 due to the lack of free charge carriers in diamond substrate 6 at normal conditions. As an example, voltage 30 (or charge) of 10 volts applied across leads 11, 12 may result in an electric field near the surface of diamond substrate 6 of approximately 10 Volts per 2 microns, or 50,000 V/cm (fifty thousand volts pre centimeter), and yet no current would flow between leads 11 and 12. "Near the surface" of diamond substrate 6 preferably is a depth of about interdigital spacing 23 (e.g., about two microns in embodiment discussed above). Depending on ambient conditions, device geometry, incident energy from radiation, and various other factors, "near the surface" depth may be less or more than interdigital spacing 23, or less or more than 2 microns in the above described embodiment, without affecting the above description.

Irradiation of substrate 6 generates charge carriers in substrate 6 that can facilitate input charge 32 to cross interdigital spacing 23 and accumulate as output charge 33 on the output side of metal pattern 21 (at output digit 22*b*, output lead 12, and output bonding pad 14). In embodiments with diamond substrate 6 the charge carriers may have a charge mobility based on the diamond substrate's charge mobility (e.g., 2000 sq.cm/V·sec). The generated charge carriers are collected by the electric field resulting from the application of voltage 31 (e.g., V.bias, V+). In embodiments with interdigital spacing of approximately 2 microns, the charge carriers may need to travel the full 2 microns to reach an output digit 22*b* (i.e., to "clear" the device) and the charge carriers' theoretical velocity would be around 108 cm/s (100,000,000 cm/s, one hundred million centimeter per second). In practice, various effects may prevent achieving the theoretical velocity resulting in the generated charge carriers only able to attain a maximum velocity (v.max, or saturation velocity) that is lower than the theoretical velocity. In embodiments with diamond substrate 6 saturation velocity (v.max) may be as high as $10^7$ cm/s (10,000,000 cm/s, or ten million centimeter per second) or $10^{11}$ microns/s (100,000,000,000 μm/s, hundred billion microns per second). It may take the generated charges near the surface on the order of 20 picoseconds ($2\times10^{-11}$ seconds) to be collected and accumulate as output charge 33 at output lead 12 and output bonding pad 14. Charges that are generated deeper than the charges near the surface of diamond substrate 6 may recombine before accumulating at output lead 12 due to the rapid weakening of the electric filed with the depth of substrate 6.

FIG. 5 illustrates a three port bias tee device 38 used to bias a an embodiment of MSM device 10. Bias tee device 38 applies a fixed voltage 31 (V.bias) to MSM device 10 and allows output charge from MSM device 10 to be collected as output voltage (Vout) 35.

Diamond's natural radiation hardness, high saturation velocity, structural hardness, durability, and other characteristics, make diamond substrates well suited for high-energy high-speed ionizing radiation detection. Solid state detectors typically show a change in performance over prolonged exposure to radiation (continuous or from pulses), including for example, substrate deterioration due to damage to the substrate lattice after extended (and repeated) exposure to ionizing radiation. Diamond crystalline materials naturally have a high radiation hardness and the lattice of diamond substrate 6 may experience less damage from irradiation, resulting in slower performance degradation from ionizing radiation than other materials that may need to radiation hardening to slow degradation from exposure. Diamond substrate 6 also may result in size reduction of device 10 (e.g., thinner substrate), for example, because embodiments with diamond substrate 6 collect generated charges that are near the surface of substrate 6 (approximately at depth of about one interdigital space 23), while deeper charges may not be collected, and may not affect the operation of device 10.

Figure 6:
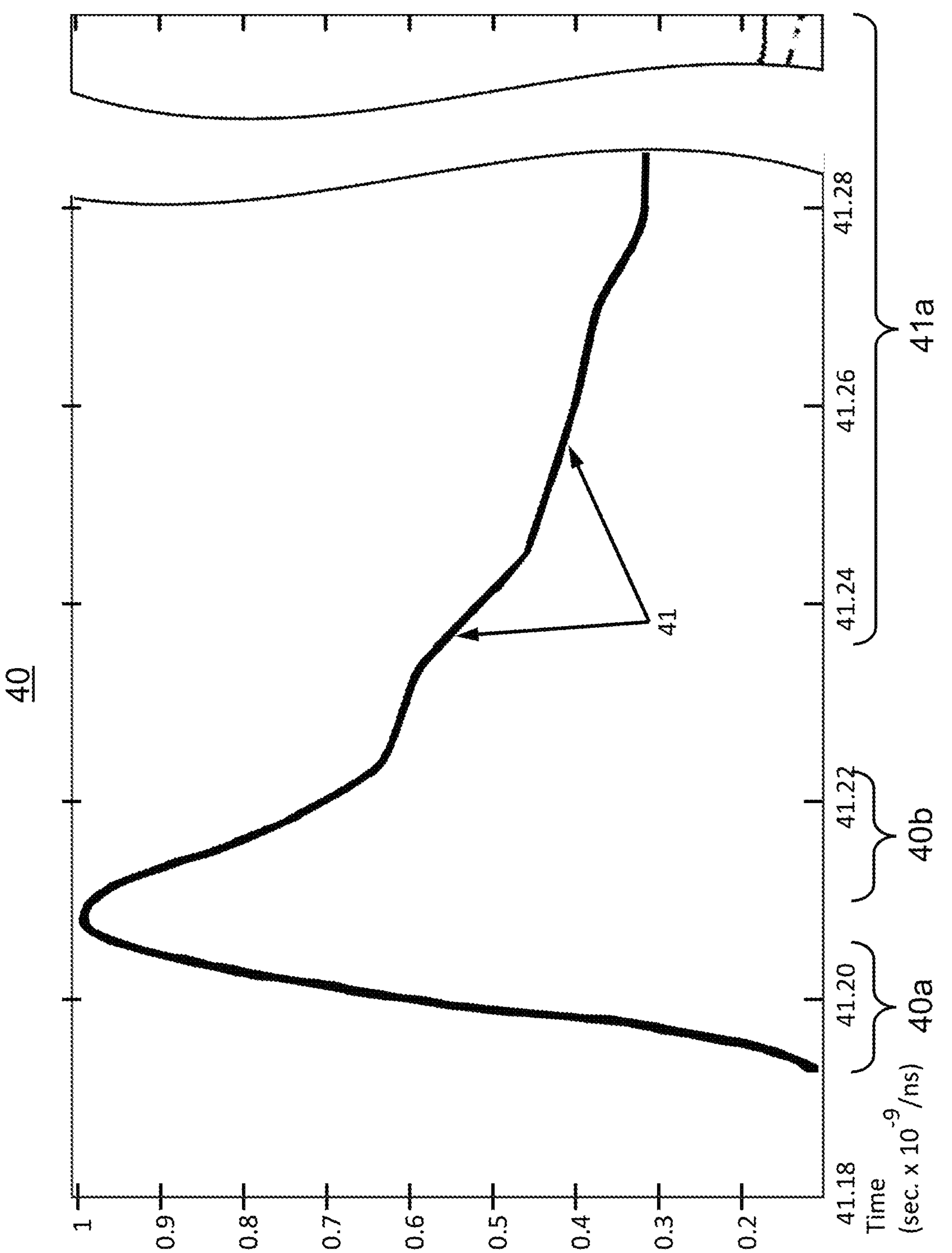
FIG. 6 is a diagram illustrating an exemplary response of a solid state detector.

Response time 40 of MSM device 10 may comprise a fast rise time 40_a_, a fast initial fall time 40_b_, and a lingering tail time 41_a_. Lingering tail 41 may result in a long tail time 41_a_ (long, relative to radiation pulse) to return to a stable baseline as illustrated in FIG. 6 (adapted from a Gallium Arsenide (GaAs) MSM photodetector device response to 1 picosecond optical pulse). Response time 40, rise time 40_a_, initial fall time 40_b_ and lingering tail time 41_a_ can be adjusted by changing MSM device geometry, as explained below. Embodiments of diamond substrate 6 MSM device 10 according to the present invention may be configured to have a lingering tail time 41_a_ of several nanoseconds (e.g., 10 ns) (not shown). Because FLASH pulses nominally may be around 100 nanoseconds, a lingering tail of approximately 10 nanoseconds may not significantly alter the shape of the pulse response.

Interdigital spacing 23 effects response time 40 of device 10, or the time it takes for charge 33 to accumulate at output lead 12 in response to irradiation with ionizing radiation. Accordingly, embodiments of MSM devices 10 having different sizes of interdigital spacing 23 will have different response times 40, For example, reducing interdigital spacing 23 may, among other effects, reduce the time it takes the charges generated in the substrate to cross a smaller interdigital spacing 23, resulting in a faster accumulation of charge 33 at output lead 12, and a faster response time 42. Reduced interdigital spacing 23 may also reduce the depth at which carriers near the surface of substrate 6 will effectively be collected. For example, in diamond substrate 6 at depths larger than interdigital spacing 23 each digit pair 22_c_ approaches a dipole-like field, reducing the likelihood that charges will be collected at such substrate depths. In another example, increasing interdigital spacing 23 may cause charge carriers to travel longer across larger interdigital spacing 23 resulting in slower accumulation of charge 33 and a slower response time 43. Active region diameter 24 also may affect response time 40, as larger diameter 24_b_ may lead to a slower response time 43 due to increased capacitance within the active region, and smaller active region diameter 24_a_ may lead to a faster response time 42.

Solid state detectors comprising embodiments of MSM device 10 may overcome various challenges with conventional solids state detectors. For example, some solid state detectors may show significant non-linear responses to high dose rates of ionizing radiation (e.g., generated by a FLASH treatment sources). Synthetic Single Crystal Diamond (SSCD) detector in some configurations may exhibit a linear response over a limited ranges of radiation dose per pulse (DPP) but saturate and are ineffective at larger DPP. Other configurations of SSCD detectors achieve a more linear response over a larger range of DPP but generally sacrifice sensitivity. These issues and tradeoff suggest that charge carriers generated from irradiation may remain in trapped states within an active volume (e.g., the volume of substrate from which charges are collected) of the detector, and that such active volume continues to conduct for an extended time. Embodiments of the present invention may address such challenges by effectively reducing the active volume by, for example, collecting charges mainly from near the surface of the substrate thereby reducing the collection volume and limiting it to the interdigitated substrate region 16.

Figure 7:
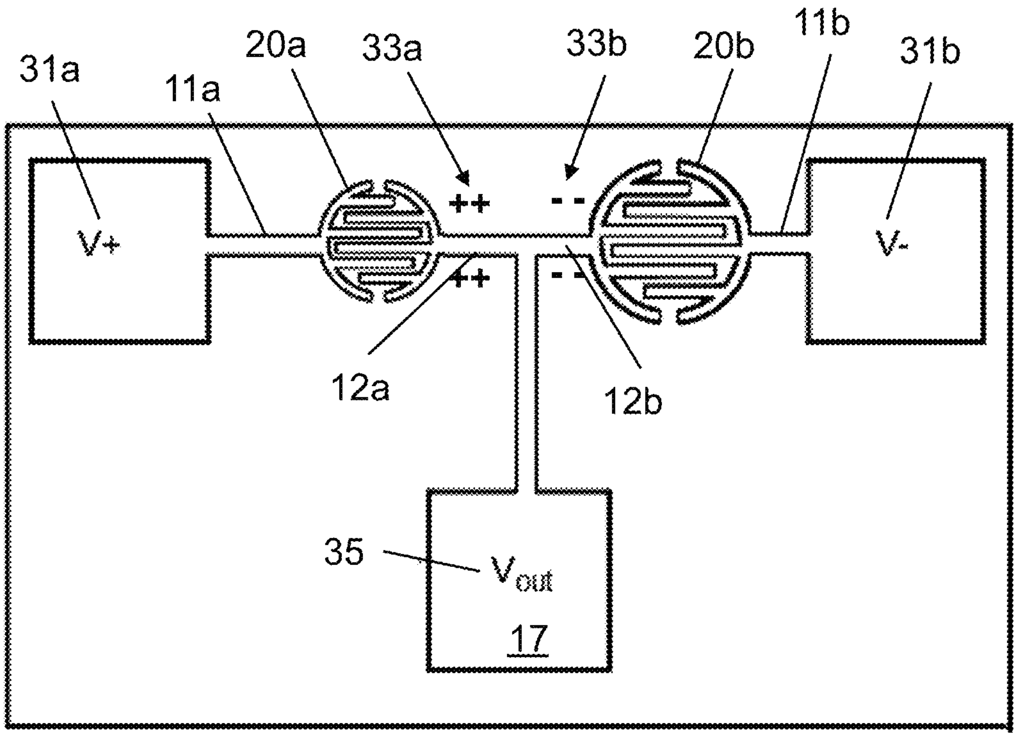
FIG. 7 is an illustration of an differential detector according to an embodiment of the present invention.
Figure 8:
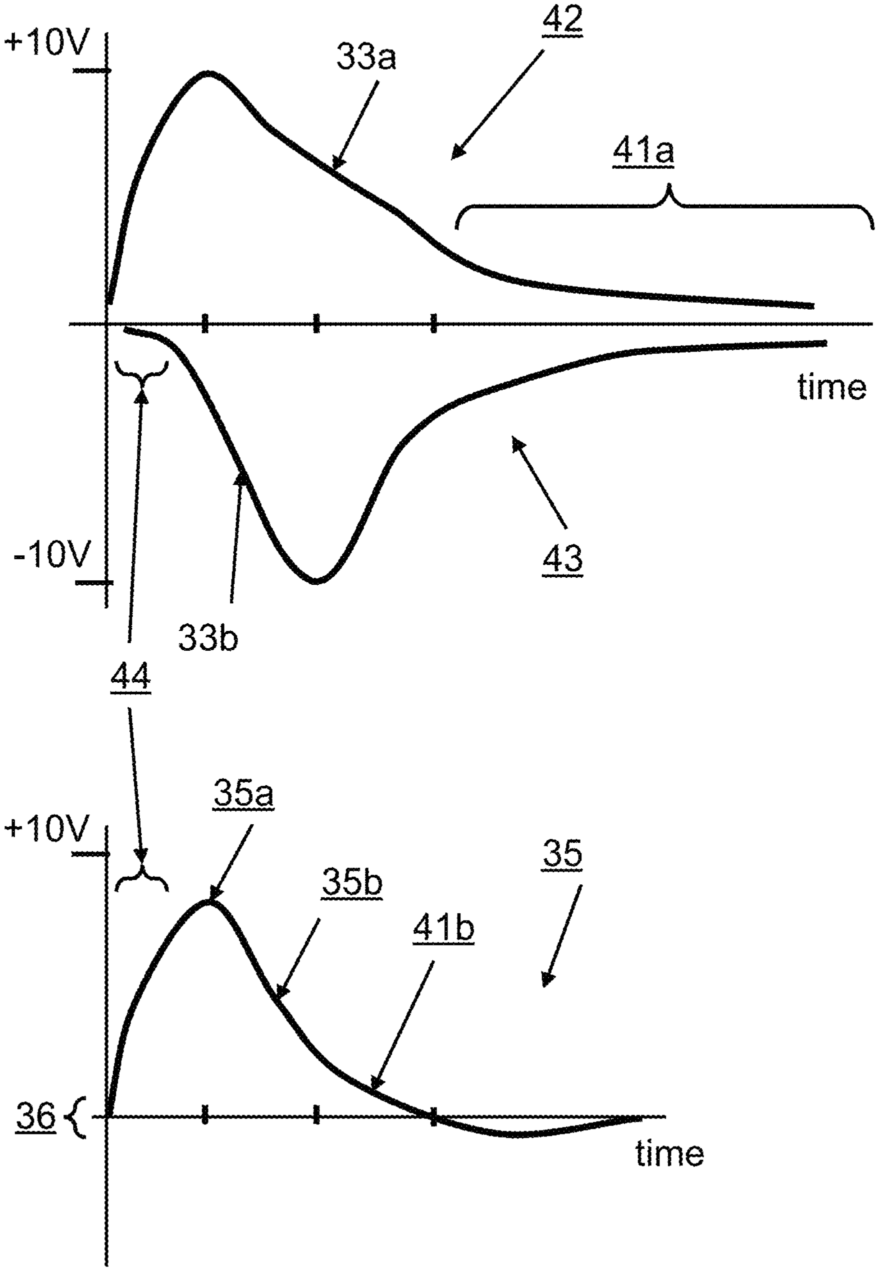
FIG. 8 is a diagram illustrating response to ionizing radiation of an embodiment of the present invention.

FIG. 7 illustrates an embodiment of a differential solid state detector (differential SSD) 1 for radiation comprising two active regions 20_a_, 20_b_. First active region 20_a_ and second active region 20_b_ each having dissimilar physical characteristics. For example, first active region 20_a_ may have a smaller first diameter 24_a_ and smaller first interdigital spacing 23_a_, and the second active region may have a larger second diameter 24_b_ and a larger interdigital spacing 23_b_. Other physical characteristics also may be different, for example digit widths 25, as well as others. At rest, when not irradiated, no current flows across active region 20_a_ and 20_b_, output electrode 17 will be balanced, and output voltage 35 can be maintained at a constant voltage 36. FIG. 8 exemplifies (not to scale) how an embodiment of a differential SSD 1 may respond when exposed to ionizing radiation.

Due to the difference in physical characteristics of the two active regions 20_a_, 20_b_, the rise time and tail characteristics will be different for each active region 20_a_, 20_b_. For example larger second diameter 24_b_ may increase the capacitance of second active region 20_b_ and wider pitch 23_b_ may increase the interdigital travel time of charged particles in second active region 20_b_. Accordingly, in the example of FIG. 8, second active region 20_b_ will have a second response time 43 that is slower than the first response time 42 of first active region 20_a_. Balanced voltages 31_a_, 31_b_ may be applied to the first and second active regions 20_a_, 20_b_, for example first input voltage 31_a_ (V+) applied to input lead 11_a_ and second input voltage (V−) applied to input lead 11_b_, where V+ and V− in this example may have equal magnitudes but opposite signs (e.g., +10V, −10V). For example, voltages 31_a_, 31_b_ may be supplied by an external power source (not shown) and applied to the contacts of a chip 4 when differential SSD 1 is packaged into chip 4, as shown in FIG. 3, or a power source may be supplied internal to a package comprising one or more devices 1.

In such embodiment peak output charges 33*a*, 33*b* accumulated at output lead 12*a* and output lead 12*b* (resulting from the current from the generated carriers) in response to a FLASH pulse may be of equal magnitude but opposite sign. Also, first charge 33*a* may accumulate at the first response time 42 and second charge 33*b* at second response time 43. Output voltage 35 at output electrode 17 (connected to first and second output leads 12*a* and 12*b*) will then represent the difference of two time resolved signals, or, the sum over time of first and second output charges 33*a* and 33*b*, which have opposite signs, and each accumulating at different response times 42 and 43. The response from first active region 20*a* and second active region 20*b* will have different rise times, lingering tail characteristics, lingering tail times, and opposite signs as illustrated in FIG. 8. The oppositely charged first and second output charges 33*a*, 33*b* also may tend to cancel each other and when combined as output voltage 35, may result in smaller peak output voltage 35*a* and a faster drop in output voltage 35*b* resulting in a faster return to a balanced constant output voltage 36. Moreover in the configuration differential SSD 1 in such embodiments enables the two oppositely charged output charges 33*a*, 33*b* to drain any residual charges remaining in the first active region 20*a* or second active region 20*b*. Differential solid state device 1 thus has a greatly reduced detector saturation, and a short tail 41*b* that may be substantially shorter than lingering tail 41, or short tail 41*b* may effectively be non-existent. During a response delay time 44 (or for simplicity "delay" 44) resulting from the difference in first and second response times 42 and 43, output voltage 35 may generally rise commensurate with the faster, first response time 42 until the second active region 20*b* begins to effectively slow down the rise from the contribution of charge 33*b* based on second, slower, response time 43. Depending on the configuration of the two active regions 20*a* and 20*b*, peak output voltage 35*a* may be reached after delay 44 (as shown in FIG. 8), during delay 44. By taking into account the magnitudes and signs of first and second charges 33*a* and 33*b*, output voltage 35 and peak output voltage 35*a* may be used as representative of the magnitude of incident ionizing radiation 39. The faster return of output voltage to a constant value 36 (illustrated in FIG. 8 as around zero volts), and the short tail 41 (or not existent tail) may facilitate detection of faster and/or stronger radiation pulses.

While the invention has been described with reference to exemplary embodiments, it will be understood by those skilled in the art that various changes, omissions, and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiments disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

The invention claimed is:

1. A solid state detector for ionizing radiation comprising:
a substrate;
a metal layer deposited on the substrate, the metal layer being electrically conductive;
a first active region connected to a first input lead and a first output lead;
a second active region connected to a second input lead and a second output lead; and,
an output electrode;
wherein the first active region, the first input lead, the first output lead, the second active region, the second input lead, the second output lead, and the output electrode are formed in the metal layer;
wherein the first output lead, the second output lead, and the output electrode are electrically connected;
wherein the first active region is configured to have a first response time when irradiated with ionizing radiation and the second active region is configured to have a second response time when irradiated with the ionizing radiation;
wherein a first voltage is applied to the first input lead and a second voltage is applied to the second input lead;
wherein the first voltage is positive, the second voltage is negative, and the first voltage and the second voltage have an equal magnitude;
wherein the solid state detector is configured, when not being irradiated with ionizing radiation, to:
maintain an output voltage at a constant level at the output electrode;
prevent the first active region from accumulating a first charge on the first output lead; and,
prevent the second active region from accumulating a second charge on the second output lead;
wherein the solid state detector is configured, when being irradiated with ionizing radiation, to:
cause the first output lead to accumulate the first charge at the first response time and the second output lead to accumulate the second charge at the second response time; and,
output a time resolved sum of the first charge and the second charge as the output voltage at the output electrode;
wherein the first charge is positive and the second charge is negative; and,
wherein, when the ionizing radiation is removed, the solid state detector is configured to:
enable one of the first charge or the second charge to drain a residual charge from the first active region and the second active region; and,
return the output voltage to the constant level.

2. The solid state detector of claim 1,
wherein the first active region comprises a first metal pattern of digits having a first digit width and a first interdigital spacing;
wherein the first metal pattern is electrically connected to the first input lead and the first output lead;
wherein the second active region comprises a second metal pattern of digits having a second digit width and a second interdigital spacing;
wherein the second metal pattern is electrically connected to the second input lead and the second output lead;
wherein the substrate is configured to:
be an insulator when the solid state detector is not being irradiated; and,
generate electrical charge carriers in the substrate when the solid state detector is irradiated with ionizing radiation; and,
wherein the first response time is faster than the second response time.

3. The solid state detector of claim 2, wherein the second active region is larger than the first active region.

4. The solid state detector of claim 3, wherein the second interdigital spacing is larger than the first interdigital spacing.

5. The solid state detector of claim 4, wherein the first active region has a first diameter, and the second active region has a second diameter; and, wherein the second diameter is larger than the first diameter.

6. The solid state detector of claim 3, wherein the output voltage is representative of an amount of the ionizing radiation incident on the solid state detector during a delay time; and, wherein the delay time is a time difference between the first response time and the second response time.

7. The solid state detector of claim 6, wherein the substrate is a diamond substrate, and the first metal pattern of digits and the second metal pattern of digits comprise gold.

8. The solid state detector of claim 7, wherein the metal layer is deposited on the substrate through electron beam deposition.

* * * * *